(12) United States Patent
Craig et al.

(10) Patent No.: US 10,159,507 B2
(45) Date of Patent: Dec. 25, 2018

(54) DEVICES, SYSTEMS, AND METHODS FACILITATING INSERTION AND REMOVAL OF COMPONENTS FROM SURGICAL INSTRUMENTS

(71) Applicant: COVIDIEN LP, Mansfield, MA (US)

(72) Inventors: Jason L. Craig, Loveland, CO (US); Scott N. Lacosta, Lafayette, CO (US); Kenneth E. Netzel, Loveland, CO (US); Clifford D. Owens, Denver, CO (US); James R. Fagan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 143 days.

(21) Appl. No.: 15/296,308

(22) Filed: Oct. 18, 2016

(65) Prior Publication Data

US 2017/0112525 A1    Apr. 27, 2017

Related U.S. Application Data

(60) Provisional application No. 62/246,745, filed on Oct. 27, 2015.

(51) Int. Cl.
*A61B 17/32* (2006.01)
*A61B 17/00* (2006.01)

(52) U.S. Cl.
CPC .......... *A61B 17/320092* (2013.01); *A61B 2017/0023* (2013.01); *A61B 2017/00526* (2013.01); *A61B 2017/00734* (2013.01)

(58) Field of Classification Search
CPC .... A61B 17/320092; A61B 2017/0023; A61B 2017/00526; A61B 2017/00734;

(Continued)

(56) References Cited

U.S. PATENT DOCUMENTS 1,864,168 A    6/1932  Bridge
1,867,632 A    7/1932  Roche
(Continued)

FOREIGN PATENT DOCUMENTS

CN    2915038 Y    6/2007
EP    2620117 A1   7/2013

OTHER PUBLICATIONS

Extended European Search report issued in corresponding application No. 16195783.2 dated Mar. 31, 2017.

*Primary Examiner* — Tuan V Nguyen

(57) ABSTRACT

A removable component configured for insertion into an internal compartment of a surgical instrument is provided including a housing defining first and second ends, a grasping member, and a biasing member. The grasping member is operably coupled to the housing at the second end thereof and is movable relative to the housing between a presented position, wherein at least a portion of the grasping member is spaced-apart from the second end of the housing, and a stored position, wherein the grasping member is approximated relative to the second end of the housing. The biasing member is disposed between the grasping member and the second end of the housing and is configured to bias the grasping member towards the presented position. Systems including a surgical instrument and such a removable component and methods of assembling a surgical instrument using the same are also provided.

14 Claims, 8 Drawing Sheets

(58) Field of Classification Search
CPC ............. H01M 2/1022; H01M 2/1016; H01M 2/1055; H01M 2/1066; H01M 2/1027; H01M 2/103
See application file for complete search history.

(56) References Cited

U.S. PATENT DOCUMENTS

| | | |
|---|---|---|
| 6,012,665 A | 1/2000 | Olona |
| 6,022,638 A | 2/2000 | Horton et al. |
| 6,257,351 B1 | 7/2001 | Ark et al. |
| 6,955,864 B1 | 10/2005 | Vaisnys et al. |
| 8,084,154 B2 | 12/2011 | Scheucher |
| 8,402,683 B2 | 3/2013 | Cabahug et al. |
| 8,758,342 B2 | 6/2014 | Bales et al. |
| 2003/0149424 A1 | 8/2003 | Barlev et al. |
| 2006/0206100 A1* | 9/2006 | Eskridge ............ A61B 17/1624 606/1 |
| 2010/0198220 A1 | 8/2010 | Boudreaux et al. |
| 2011/0022032 A1 | 1/2011 | Zemlok et al. |
| 2012/0110810 A1* | 5/2012 | Houser ............ A61B 17/00234 29/271 |
| 2013/0330589 A1 | 12/2013 | Detry et al. |
| 2015/0080660 A1 | 3/2015 | Gomez et al. |

\* cited by examiner

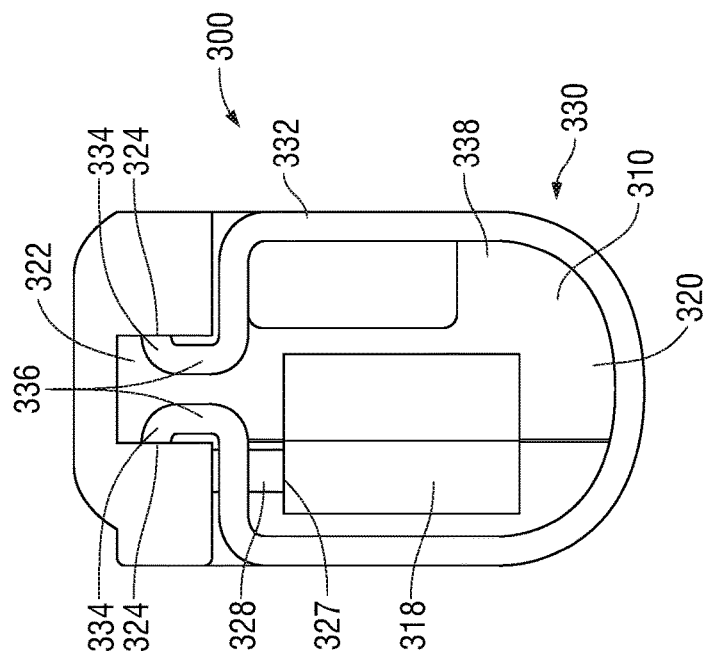
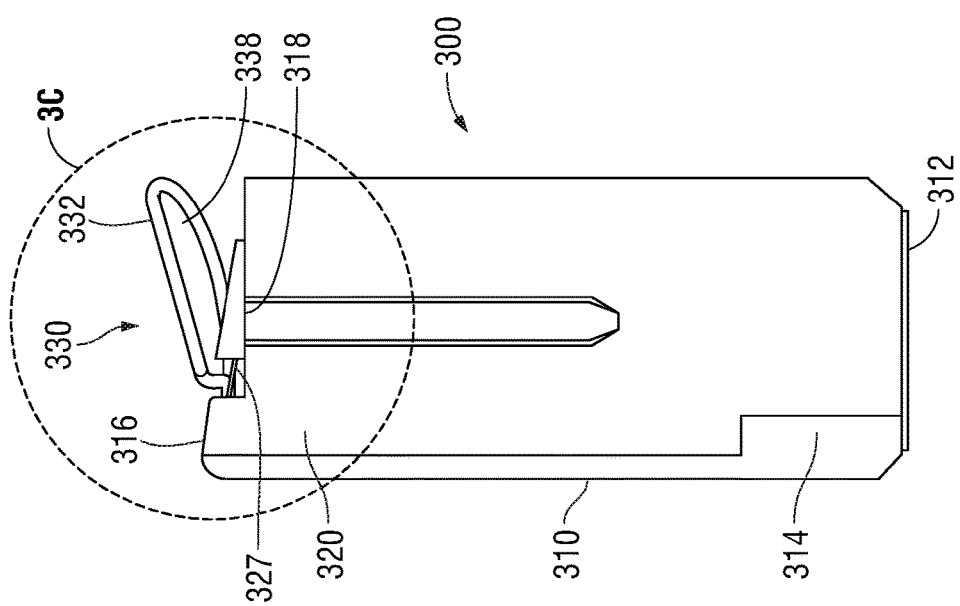

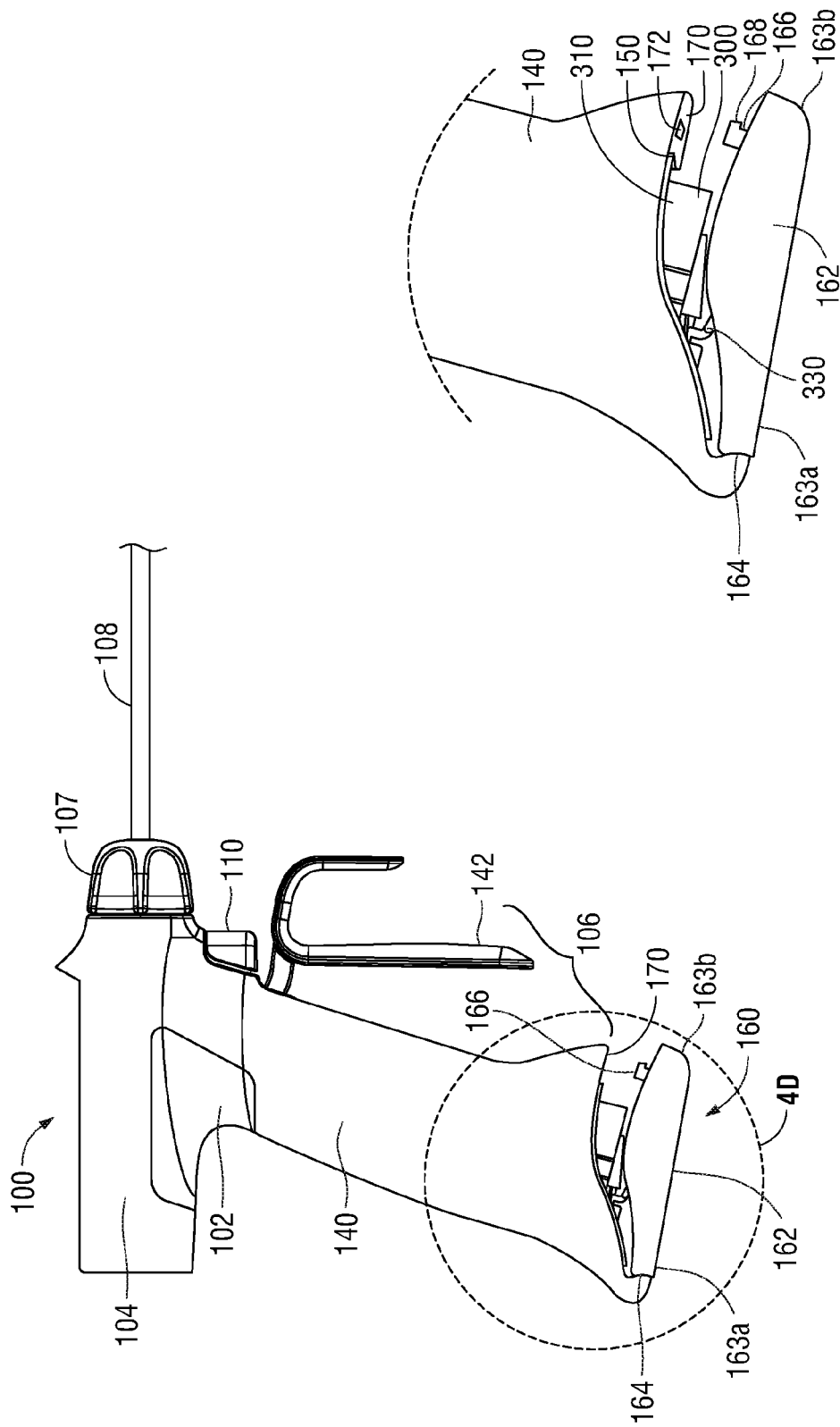

DEVICES, SYSTEMS, AND METHODS FACILITATING INSERTION AND REMOVAL OF COMPONENTS FROM SURGICAL INSTRUMENTS

CROSS REFERENCE TO RELATED APPLICATION

The present application claims the benefit of and priority to U.S. Provisional Application Ser. No. 62/246,745, filed on Oct. 27, 2016, the entire contents of which are incorporated herein by reference.

BACKGROUND

Technical Field

The present disclosure relates to devices, systems, and methods facilitating the insertion and removal of components from within a sealed compartment of a surgical instrument.

Background of Related Art

Untethered surgical instruments are advantageous in that they obviate the need for cables coupling the instrument to external inputs by incorporating these input components onto and/or into the instrument itself. Accordingly, a number of surgical instrument manufacturers have developed untethered and/or partially untethered energy-based surgical instruments, powered surgical instruments, and the like. In many instances, such surgical instruments include a disposable that is configured to receive one or more reusable components, e.g., battery packs, controllers, motor assemblies, generators, transducers, combinations thereof, etc., that replace the need for traditional tethered connections to external inputs.

Due to the requirement of sterility within the surgical field, all components of surgical instruments must either be sterilized or sealed within a sterile compartment of the surgical instrument. With regard to sealing non-sterile components within a sterile compartment, care must be taken to ensure the sterile field is not contaminated. Accordingly, it would be beneficial to provide devices, systems, and methods that facilitate the insertion and removal of reusable components, e.g., battery packs, controllers, motor assemblies, generators, transducers, combinations thereof, etc., from sealed compartments of surgical instruments without compromising the sterile surgical field.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a removable component configured for insertion into an internal compartment of a surgical instrument includes a housing defining a first end and a second end, a grasping member, and a biasing member. The grasping member is operably coupled to the housing at the second end thereof, and is movable relative to the housing between a presented position, wherein at least a portion of the grasping member is spaced-apart from the second end of the housing, and a stored position, wherein the grasping member is approximated relative to the second end of the housing. The biasing member is disposed between the grasping member and the second end of the housing and is configured to bias the grasping member towards the presented position.

In an aspect of the present disclosure, the removable component is a battery pack including at least one electrical contact disposed at the first end thereof.

In another aspect of the present disclosure, the grasping member is pivotably coupled to the housing via a hinge.

In yet another aspect of the present disclosure, the grasping member includes a finger ring portion, at least one hinge leg, and an extension portion interconnecting the finger ring portion and the at least one hinge leg.

In still another aspect of the present disclosure, the housing includes a hinge block defining at least one lumen. The at least one hinge leg is pivotably disposed within the at least one lumen to enable pivoting of the grasping member relative to the housing.

In another aspect of the present disclosure, the housing includes a retainer block. In such aspects, the biasing member is partially-disposed within the retainer block.

In still yet another aspect of the present disclosure, an exposed portion of the biasing member extends from the retainer block. The exposed portion of the biasing member is configured to contact the finger ring portion of the grasping member upon movement of the grasping member towards the stored position to bias the grasping member against further movement towards the stored position.

In another aspect of the present disclosure, in the stored position of the grasping member, the finger ring portion is disposed about the retainer block in surrounding relation therewith.

A surgical system provided in accordance with aspects of the present disclosure includes a surgical instrument and a removable component. The surgical instrument defines an internal compartment and a door movable between an open position and a closed position for providing access to the internal compartment and closing the internal compartment. The removable component includes a housing defining a first end and a second end, a grasping member, and a biasing member. The housing is configured for insertion into the internal compartment of the surgical instrument led by the first end thereof. The grasping member is operably coupled to the housing at the second end thereof and is movable relative to the housing between a presented position, wherein at least a portion of the grasping member is spaced-apart from the second end of the housing, and a stored position, wherein the grasping member is approximated relative to the second end of the housing. The biasing member is disposed between the grasping member and the second end of the housing and is configured to bias the grasping member towards the presented position. As a result of the above-detailed configuration, upon moving the door of the surgical instrument to the closed position with the removable component disposed within the internal compartment, the door urges the grasping member towards the stored position against the bias of the biasing member.

In an aspect of the present disclosure, the surgical instrument further includes a lock assembly configured to lock the door in the closed position upon movement of the door to the closed position.

In another aspect of the present disclosure, with the door locked in the closed position with the removable component disposed within the internal compartment, the biasing member is disposed in a loaded state.

In still another aspect of the present disclosure, the lock assembly further includes a release button that is selectively depressible to unlock the door from the closed position.

In yet another aspect of the present disclosure, upon depression of the release button to unlock the door, the grasping member is configured to bias the grasping member towards the presented position, thereby urging the door towards the open position.

In still yet another aspect of the present disclosure, the removable component is a battery pack configured to provide power to the surgical instrument. The battery pack may further include at least one electrical contact disposed at the first end thereof and configured to electrically couple to a corresponding at least one electrical contact of the surgical instrument upon insertion of the removable component into the internal compartment.

In another aspect of the present disclosure, the grasping member of the removable component includes a finger ring portion configured to facilitate manipulation of the removable component.

A method of assembling a surgical instrument provided in accordance with the present disclosure includes moving a door of a surgical instrument from a closed position to an open position to provide access to an internal compartment of the surgical instrument. The method further includes inserting a removable component into the internal compartment, the removable component including a grasping member movable between a presented position and a stored position and biased towards the presented position by a biasing member. The method further includes moving the door of the surgical instrument from the open position to the closed position with the removable component disposed within the internal compartment such that the door urges the grasping member towards the stored position against the bias of the biasing member to at least partially load the biasing member. The method additionally includes releasing the door from the closed position. Upon release of the door from the closed position, the at least partially loaded biasing member urges the grasping member towards the presented position, the grasping member in turn urging the door towards the open position.

In an aspect of the present disclosure, moving the door of the surgical instrument from the open position to the closed position includes locking the door in the closed position.

In another aspect of the present disclosure, releasing the door from the closed position includes depressing a release button to unlock the door from the closed position.

In still another aspect of the present disclosure, the method further includes grasping the grasping member and withdrawing the removable component from the internal compartment via the grasping member.

BRIEF DESCRIPTION OF THE DRAWINGS

Various aspects and features of the present disclosure are described hereinbelow with reference to the drawings wherein like numerals designate identical or corresponding elements in each of the several views:

FIG. 3A is a side, perspective view of the battery pack of FIG. 2;

FIG. 3B top, perspective view of the battery pack of FIG. 2;

FIG. 4C is a side, perspective view illustrating closure of the compartment door of the disposable handle of the surgical instrument of FIG. 1 with the battery pack positioned therein;

FIG. 4D is an enlarged, side, perspective view of the area of detail identified as "4D" in FIG. 4C.

DETAILED DESCRIPTION

Figure 1:
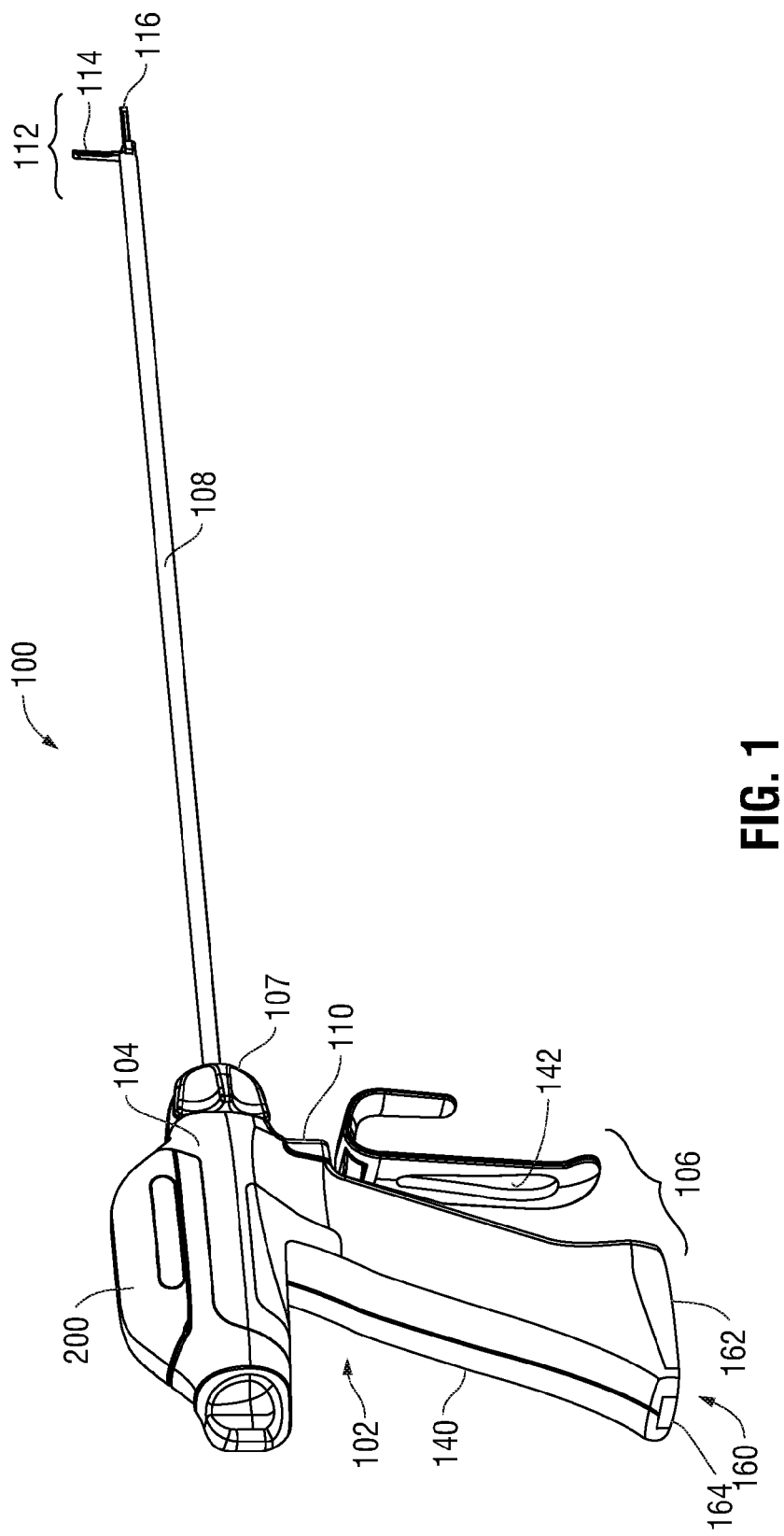
FIG. 1 is a rear, side, perspective view of an exemplary untethered surgical instrument provided in accordance with the present disclosure.
Figure 2:
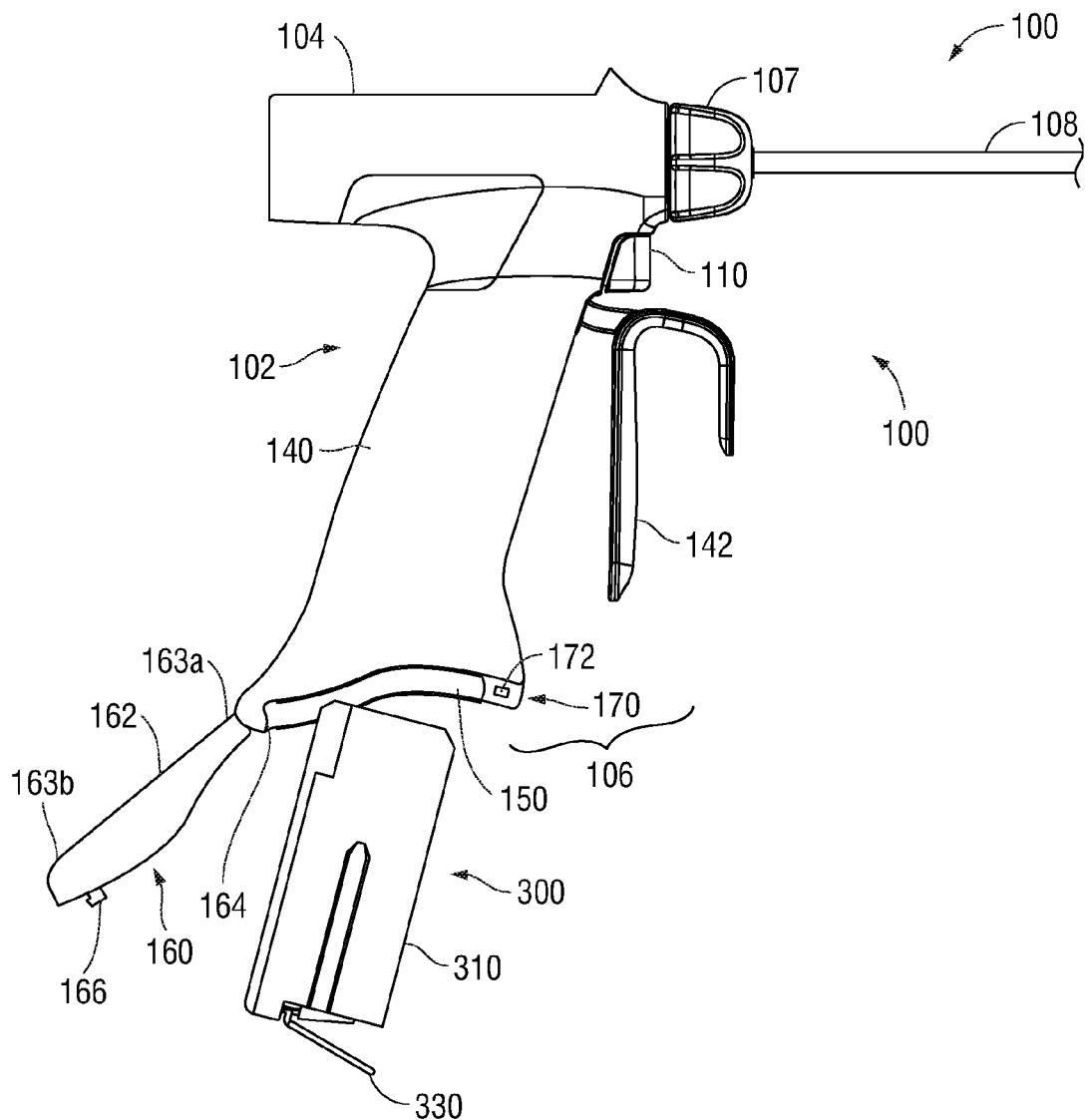
FIG. 2 is a side, perspective view of the disposable handle of the surgical instrument of FIG. 1 with a battery pack removed from the battery compartment of the disposable handle.

FIGS. 1 and 2 depict an untethered ultrasonic surgical instrument 100 provided in accordance with the aspects and features of the present disclosure. Ultrasonic surgical instrument 100 is configured to releasably mount a transducer and generator assembly ("TAG") 200 thereon and to releasably enclose a battery pack 300 within a sealable battery compartment 150 thereof. Although detailed hereinbelow with regard to the insertion and removal of battery pack 300 from sealable battery compartment 150 of ultrasonic surgical instrument 100, the aspects and features of the present disclosure are equally applicable for use with any other removably insertable component of ultrasonic surgical instrument 100 or any other suitable surgical instrument configured to removable receive one or more components. Obviously, different considerations apply to each particular type of instrument and removable component; however, the aspects and features of the present disclosure are equally applicable and remain generally consistent with respect to any such surgical instrument or removable component. For the purposes herein, untethered ultrasonic surgical instrument 100 is generally described.

Continuing with reference to FIGS. 1 and 2, ultrasonic surgical instrument 100 generally includes a sterile disposable 102 including a housing 104, a handle assembly 106, a rotating assembly 107, a shaft 108, an activation button 110, and an end effector assembly 112. Non-sterile, reusable battery pack 300 is releasably insertable into battery compartment 150 defined within handle assembly 106 of disposable 102. Sterilizable, reusable TAG 200 is releasably mountable on housing 104 of disposable 102. However, it is also contemplated that, rather than mounting on housing 104, TAG 200 be configured for releasably insertion into a TAG compartment defined within housing 104, similarly as detailed below with respect to the releasable insertion of battery pack 300 into battery compartment 150. Handle assembly 106, as also will be detailed below, further includes a door assembly 160 having a lock assembly 170 (FIG. 5) associated therewith for releasably securing and sealing battery pack 300 within battery compartment 150.

Shaft 108 of ultrasonic surgical instrument 100 is coupled to housing 104 at a proximal end of shaft 108 and extends distally from housing 104. End effector assembly 112 is disposed at a distal end of shaft 108 and includes first and second jaw members 114, 116, one or both of which is movable relative to the other, e.g., upon actuation of movable handle 142 of handle assembly 106, between an open position and a clamping position for grasping tissue therebetween. One of the jaw members, e.g., jaw member 116, is configured to serve as an active or oscillating ultrasonic blade that is selectively activatable to ultrasonically treat tissue grasped between jaw members 114, 116. More specifically, TAG 200 is configured to convert electrical energy provided by battery pack 300 into mechanical energy that produces motion at the end of a waveguide (not shown), e.g., at jaw member 116. The electronics (not shown) of TAG 200 convert the electrical energy provided by battery pack 300 into a high voltage AC waveform that drives the transducer (not shown) of TAG 200. When the transducer and the waveguide are driven at their resonant frequency, mechanical motion, e.g., ultrasonic motion, is produced at the active jaw member 116 for treating tissue grasped between jaw members 114, 116. Activation button 110 is disposed on housing 104 and is selectively activatable in a first position and a second position to supply electrical energy from battery pack 300 to TAG 200 for operating ultrasonic surgical instrument 100 in a low-power mode of operation and a high-power mode of operation, respectively.

Figure 3C:
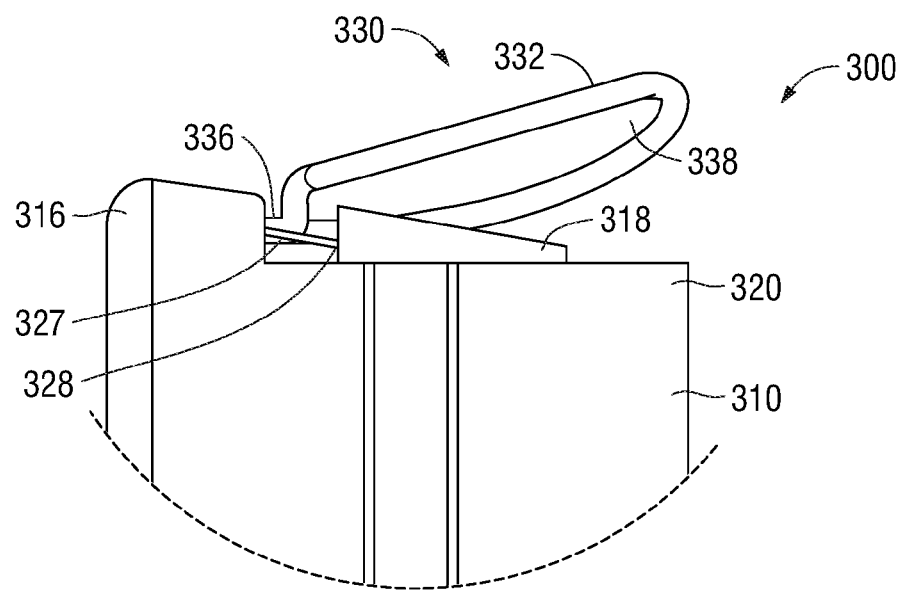
FIG. 3C is an enlarged, side, perspective view of the area of detail identified as "3C" in FIG. 3B.
Figure 3D:
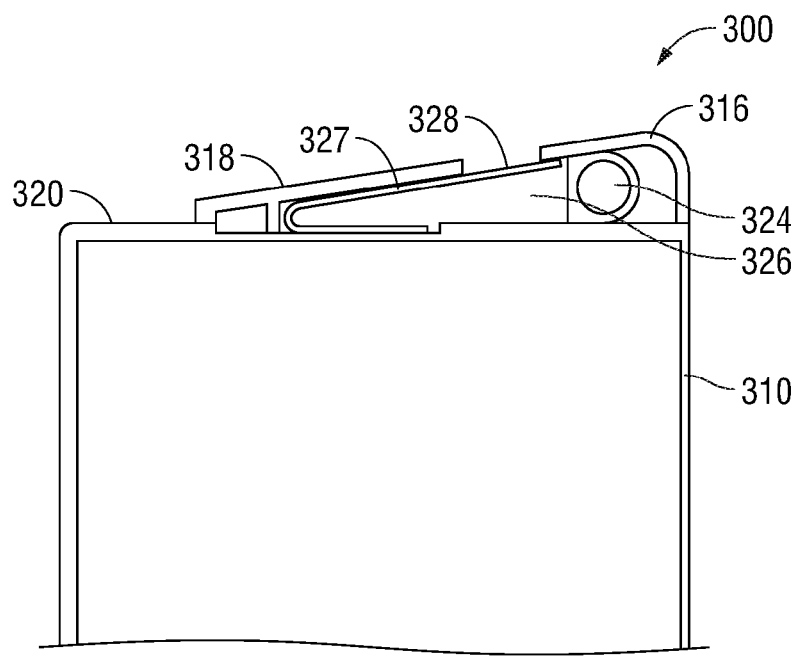
FIG. 3D is a side view into the interior of a portion of the housing of the battery pack of FIG. 2.

Referring to FIG. 2 in particular, handle assembly 106 includes a fixed handle 140 that is integral with housing 104 and movable handle 142 which is operably coupled to end effector 112 (FIG. 1) and movable relative to fixed handle 140 between a spaced-apart position and a compressed position to move jaw members 114, 116 (FIG. 1) between the open position and the clamping position. Fixed handle 140 includes a hollow interior portion so as to define battery compartment 150 therein, and an open free end 152 to enable insertion and removal of battery pack 300 into battery compartment 150. Fixed handle 140 supports internal contacts (not shown) within battery compartment 150 of handle assembly 106 that are configured to mate with corresponding contacts 312 (FIG. 3A) of battery pack 300 upon insertion of battery pack 300 into battery compartment 150. As such, power and/or control signals can be relayed between battery pack 300 and TAG 200, which likewise includes contacts (not shown) configured to mate with corresponding internal contacts (not shown) of housing 104 of disposable 102 upon engagement of TAG 200 therewith.

Figure 5:
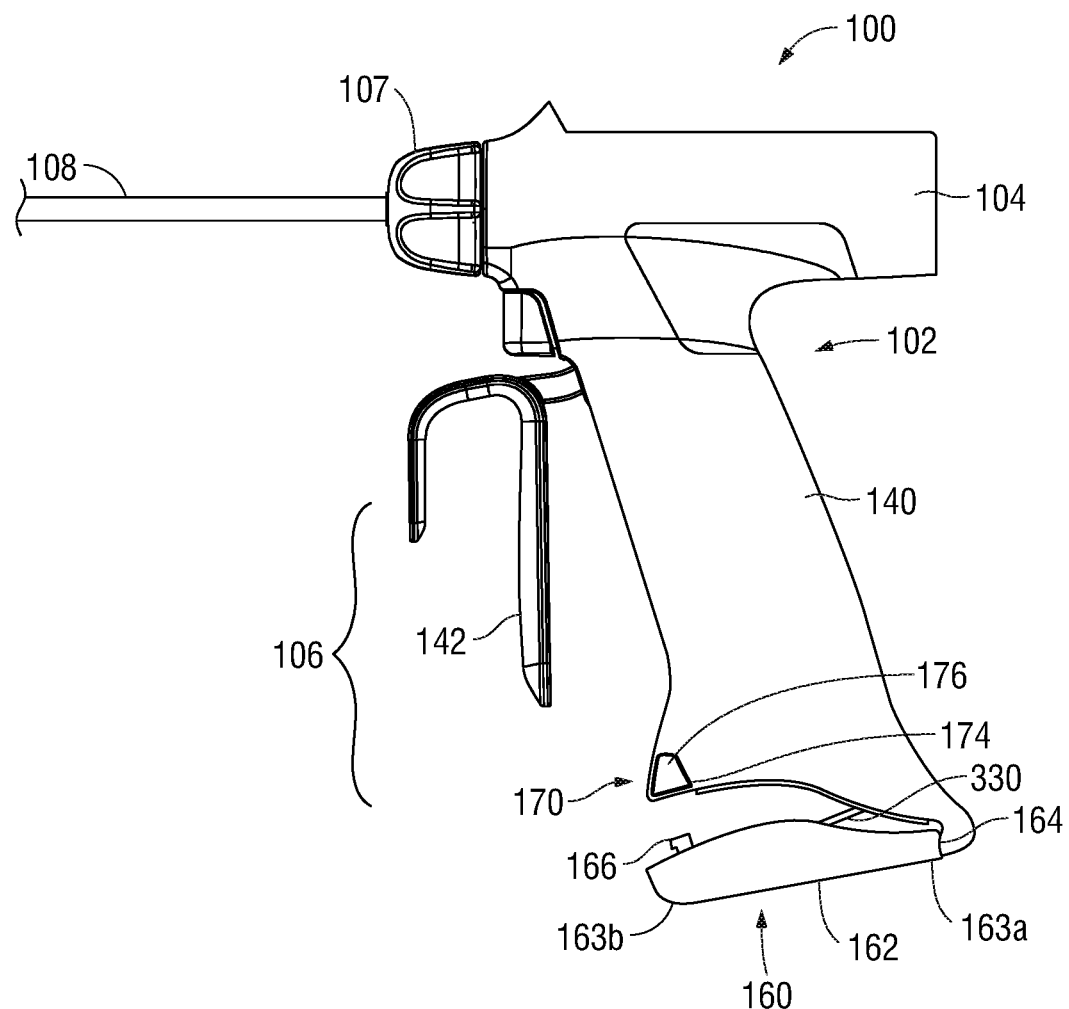
FIG. 5 is a side, perspective view illustrating opening of the compartment door of the disposable handle of the surgical instrument of FIG. 1.

With additional reference to FIGS. 1 and 5, door assembly 160 is operably coupled to fixed handle 140 at the free end thereof and is provided to releasably enclose battery pack 300 within battery compartment 150 of fixed handle 140, sealing battery pack 300 therein and maintaining contacts 312 (FIG. 3A) of battery pack 300 in communication with the internal contacts (not shown) of battery compartment 150. Door assembly 160 includes a door 162 having first and second ends 163a, 163b, respectively, and a hinge 164 pivotably coupling first end 163a of door 162 with the free end of fixed handle 140 adjacent battery compartment 150. Door 162 is pivotable about hinge 164 from an open position (FIG. 2), providing access to battery compartment 150 for the insertion and removal of battery pack 300 therefrom, and a closed position (FIG. 1), releasably enclosing and sealing battery pack 300 within battery compartment 150.

Door 162 further includes a locking foot 166 disposed towards second end 163b thereof. Locking foot 166 includes an outwardly-extending tab 168 disposed at the free end thereof and is configured to lock in engagement with lock assembly 170 to releasably secure door 162 in the closed position. More specifically, upon pivoting of door 162 to the closed position, locking foot 166 is inserted into locking aperture 172 of lock assembly 170, which is defined within fixed handle 140 adjacent battery compartment 150. Locking aperture 172 is configured to urge tab 168 of locking foot 166 to initially flex inwardly upon insertion into locking aperture 172. Upon full insertion of locking foot 166 into locking aperture 172, tab 168 is moved into position adjacent window 174, which is defined within fixed handle 140 and in communication with locking aperture 172, thus permitting tab 168 to resiliently return to its initial or un-flexed position. The return of tab 168 to its initial or un-flexed position extends tab 168 at least partially into window 174, thereby locking door 162 in the closed position.

A release button 176 of lock assembly 170 is disposed within window 174. Release button 176 is selectively depressible and configured such that, upon depression of release button 176 inwardly into window 174, release button 176 contacts tab 168 and urges tab 168 to flex inwardly, thereby disengaging tab 168 from window 174. With tab 168 disengaged from window 174, door 162 may be pivoted back to the open position to enable insertion and removal of battery pack 300 from battery compartment 150.

Referring to FIGS. 2 and 3A-3D, battery pack 300 generally includes an outer housing 310 and a grasping member 330. Outer housing 310 includes an array of contacts 312 disposed at a first end 314 thereof. A hinge block 316 and retainer block 318 are disposed at a second, opposite end 320 of outer housing 310 and may be integrally formed therewith. Outer housing 310 houses the one or more battery cells (not shown) and battery circuitry (not shown) of battery pack 300. Contacts 312 provide an interface between the internal components, e.g., the one or more battery cells and battery circuitry, of outer housing 310 of battery pack 300 and the internal contacts (not shown) of disposable 102 to enable communication of power and/or control signals between battery pack 300, TAG 200 (FIG. 1), and activation button 110 (FIG. 1). Hinge block 316 defines a slot 322 and a pair of lumens 324, each lumen 324 disposed on one side of slot 322 to enable pivotable coupling of grasping member 330 with hinge block 316 of outer housing 310, as detailed below. Retainer block 318 defines a cavity 326 retaining a portion of a biasing member 327 therein. Biasing member 327 extends from cavity 326 of retainer block 318 so as to define an exposed portion 328 of biasing member 327. Biasing member 327 is biased outwardly from second end 320 of outer housing 310 and, as detailed below, is configured such that, upon sufficient application of force to exposed portion 328 thereof, biasing member 327 is flexed inwardly towards second end 320 of housing 310 and against the bias of biasing member 327. As illustrated herein, biasing member 327 may be a flat spring, although it is also contemplated that biasing member 327 take the form of a torsion spring, plunger mechanism, etc. Further, instead of a separate biasing member 327, grasping member 330 may include biasing features to serve a similar purpose as biasing member 327.

Grasping member 330 of battery pack 300 includes a finger ring portion 332, a pair of hinge legs 334, and an extension portion 336 extending between and interconnecting finger ring portion 332 and hinge legs 334. Grasping member 330 may be formed from a single piece of wire stock wherein the ends thereof define hinge legs 334 and the body thereof is bent to define finger ring portion 332 and extension portion 336, although other configurations are also contemplated. Finger ring portion 332 defines an opening 338 configured to receive a user's finger to facilitate grasping and manipulation of battery pack 300, although other configurations suitable to facilitate grasping and/or manipulation are also contemplated. Opening 338 is also sufficiently dimensioned so as to enable positioning of finger ring portion 332 about retainer block 318 of housing 310 in surrounding relation therewith. Further, finger ring portion 332 generally approximates the dimensions of second end 320 of outer housing 310 of battery pack 300 so as not to extend outwardly therefrom. As such, finger ring portion 332 does not interfere with the insertion of battery pack 300 into battery compartment 150 of fixed handle 140 of disposable 102 (see FIG. 2).

Extension portion 336 of grasping member 330 defines a narrowed configuration as compared to finger ring portion 332 so as to enable extension portion 336 to extend into slot 322 of hinge block 316. Hinge legs 334 extend outwardly from extension portion 336 in opposite directions and are received within lumens 324 of hinge block 316 to pivotably couple grasping member 330 with housing 310. More specifically, grasping member 330 is pivotable about hinge legs 334 and relative to second end 320 of housing 310 between an presented position, wherein finger ring portion 332 is spaced-apart from second end 320 of housing 310 in a more upright position to facilitate grasping of finger ring portion 332, and a stored position, wherein finger ring portion 332 is approximated relative to second end 320 of housing 310 and positioned about retainer block 318 of housing 310 in surrounding relation therewith.

Grasping member 330 and biasing member 327 are relatively positioned such that, as grasping member 330 is pivoted about hinge legs 334 and relative to second end 320 of housing 310 from the presented position towards the stored position, finger ring portion 332 of grasping member 330 contacts biasing member 327 prior to reaching the stored position. Thus, in order to fully pivot grasping member 330 to the stored position, grasping member 330 must be sufficiently urged to overcome the bias of biasing member 327 and flex biasing member 327 towards second end 320 of housing 310. Likewise, upon removal of a holding force retaining grasping member 330 in the stored position, biasing member 327 is resiliently returned outwardly under its bias, thereby urging grasping member 330 to pivot from the stored position back towards the presented position. The spring constant and configuration of biasing member 327 as well as the relative position of biasing member 327 and grasping member 330 may be selected to achieve a desired point-at-which grasping member 330 contacts biasing member 327 and point-to-which grasping member 330 is returned under the bias of biasing member 327. It is contemplated that the positioning of grasping member 330 in the returned position, that is the point-to-which grasping member 330 is returned under the bias of biasing member 327, be sufficiently spaced-apart from second end 320 of housing 310 so as to readily enable grasping and manipulation of finger ring portion 332 of grasping member 330, e.g., to facilitate insertion and removal of battery pack 300 from battery compartment 150 of fixed handle 140 of disposable 102 (see FIG. 2).

Figure 4A:
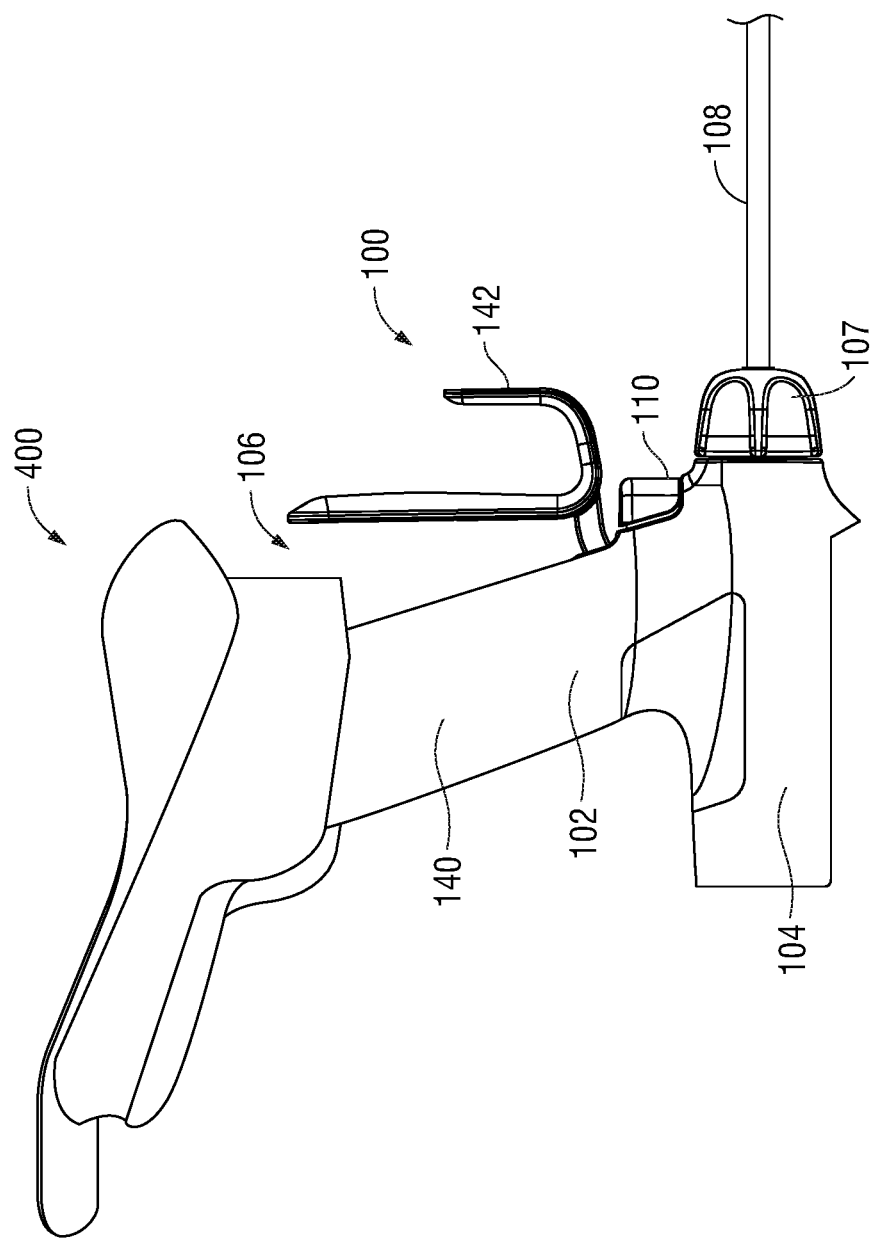
FIG. 4A is a side, perspective view illustrating an insertion guide positioned on the disposable handle of the surgical instrument of FIG. 1 in preparation for inserting the battery pack into the compartment of the disposable handle.

Turning now to FIGS. 4A-4D, the insertion of battery pack 300 into battery compartment 150 of fixed handle 140 of disposable 102 in preparation for use of ultrasonic surgical instrument 100 in a sterile surgical field is described. Initially, as illustrated in FIG. 4A, ultrasonic surgical instrument 100 is inverted, door 162 is moved to the open position exposing battery compartment 150, and an insertion guide 400 is placed over the free end of fixed handle 140 of ultrasonic surgical instrument 100. Insertion guide 400 is provided to inhibit contact between battery pack 300 and other non-sterile objects and the exterior of the sterile ultrasonic surgical instrument 100. However, it is also envisioned that battery pack 300 be inserted into battery compartment 150 without the use of insertion guide 400.

Figure 4B:
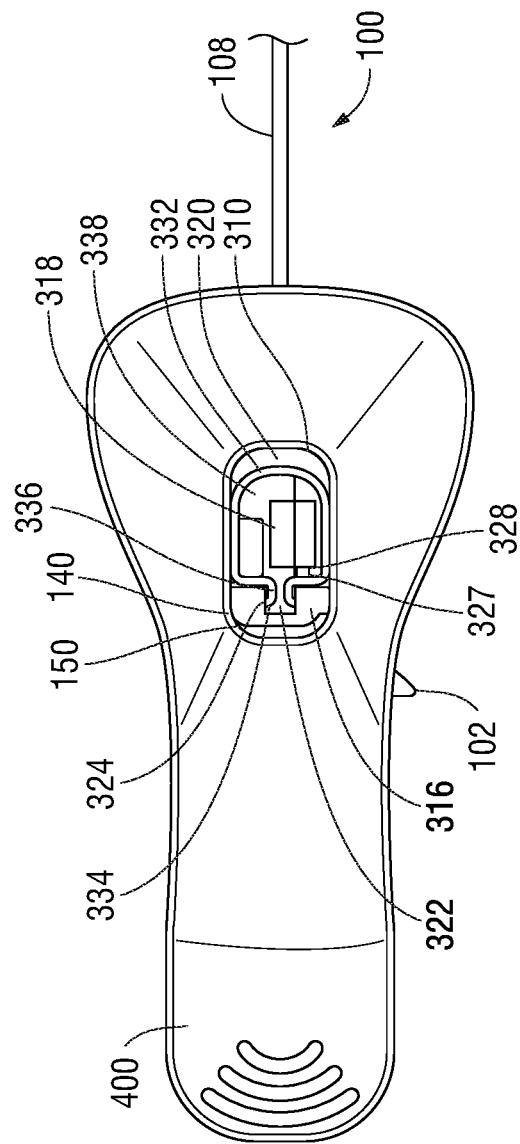
FIG. 4B is a top, perspective view illustrating the battery pack positioned within the compartment of the disposable handle after insertion through the insertion guide.

With additional reference to FIG. 4B, with ultrasonic surgical instrument 100 inverted, door 162 open, and insertion guide 400 in position, battery pack 300, led by first end 314 (FIGS. 3A-3D) thereof, is inserted through insertion guide 400 and into battery compartment 150. Insertion of battery pack 300 into battery compartment 150 may be accomplished via grasping finger ring portion 332 of grasping member 330, or in any other suitable fashion. Once battery pack 300 has been fully inserted into battery compartment 150, insertion guide 400 may be removed.

Turning also to FIGS. 4C and 4D, with battery pack 300 fully inserted into battery compartment 150, door 160 may be closed and locked to retain battery pack 300 within battery compartment 150. It is noted that, prior to closing door 160, grasping member 330 may be disposed anywhere between the presented position and the point at which finger ring portion 332 of grasping member 330 contacts biasing member 327. This is due to the fact that, as detailed above, sufficient urging of grasping member 330 must be applied to overcome the bias of biasing member 327 before grasping member 330 is enabled to move further towards the stored position.

In order to closer door 162, door 162 is rotated about hinge 164 towards the closed position. As door 162 is pivoted towards the closed position, door 162 eventually contacts grasping member 330. At this point, in order to further pivot door 162 towards the closed position, sufficient urging must be applied to door 162 to urge grasping member 330 into contact with biasing member 327 and to overcome the bias of biasing member 327. As biasing member 327 is flexed inwardly towards housing 310, grasping member 330 is permitted to pivot towards the stored position and, thus, door 162 is permitted to pivot further towards the closed position. As door 162 is pivoted further towards the closed position, locking foot 166 is inserted into locking aperture 172 and, ultimately, tab 168 of locking foot 166 is engaged within window 174 to lock door 162 in the closed position. In this closed position, the locking engagement of door 162 with lock assembly 170 retains grasping member 330 in the stored position and, thus, retains biasing member 327 in a flexed position. In other words, with battery pack 300 locked within battery compartment 150 via door 162, biasing member 327 is retained in a loaded state.

Referring to FIGS. 1 and 4A-5, prior to or after insertion of battery pack 300 into battery compartment 150 of fixed handle 140 of disposable 102, TAG 200 is engaged with housing 104 of disposable 102. With battery pack 300 and TAG 200 engaged with disposable 102, ultrasonic surgical instrument 100 is ready for use in treating tissue.

With particular reference to FIG. 5, upon completion of the desired procedure(s), or where it is necessary to remove battery pack 300, e.g., for recharging or replacement, door 162 is opened by depressing release button 176. Upon sufficient depression of release button 176, tab 168 of locking foot 166 is disengaged from window 174, thereby unlocking door 162 from the closed position. Upon unlocking of door 162, the retaining force maintaining biasing member 327 of battery pack 300 in the loaded state is removed. As such, biasing member 327 is urged back towards its at-rest position, thereby urging finger ring portion 332 of grasping member 330 of battery pack 300 to pivot from the stored position towards the grasping position. Finger ring portion 332, in turn, contacts door 162 and urges door 162 to pivot from the closed position towards the open position. As can be appreciated, this configuration not only biases door 162 open upon unlocking of door 162, but also moves finger ring portion 332 of grasping member 330 of battery pack 300 towards the presented position to facilitate grasping of finger ring portion 332 for removal of battery pack 300 from battery compartment 150.

The configurations of battery pack 300, door assembly 160, and lock assembly, as detailed above, and the above-detailed insertion and removal methods thereof, enable the insertion and removal of battery pack 300 without compromising the sterility of the surgical field or ultrasonic surgical instrument 100. More specifically, the above-detailed configurations and methods enable a user that is part of the sterile surgical field to open and close door 162 without contacting any non-sterile components, e.g., battery pack 300, the interior of door 162, or battery compartment 150. Likewise, these configurations and methods enable a user that is not part of the sterile surgical field to insert and remove battery pack 300 without contacting any sterile components, e.g., the exterior of door 162 or fixed handle 140. As such, exchange of the battery pack 300 before, during, and/or after a surgical procedure can be readily accomplished.

While several embodiments of the disclosure have been shown in the drawings and described hereinabove, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A removable component configured for insertion into an internal compartment of a surgical instrument, the removable component comprising:
    a housing defining a first end and a second end;
    a grasping member including a finger ring portion, at least one hinge leg, and an extension portion interconnecting the finger ring portion and the at least one hinge leg, the grasping member pivotably coupled to the housing at the second end of the housing via the at least one hinge leg, the grasping member pivotable about the at least one hinge leg and relative to the housing between a presented position, wherein at least a portion of the grasping member is spaced-apart from the second end of the housing, and a stored position, wherein the grasping member is approximated relative to the second end of the housing; and
    a biasing member disposed between the grasping member and the second end of the housing, the biasing member configured to bias the grasping member towards the presented position.

2. The removable component according to claim 1, wherein the removable component is a battery pack, the battery pack including at least one electrical contact disposed at the first end of the removable component.

3. The removable component according to claim 1, wherein the housing includes a hinge block defining at least one lumen, the at least one hinge leg pivotably disposed within the at least one lumen to enable pivoting of the grasping member relative to the housing.

4. The removable component according to claim 1, wherein the housing includes a retainer block, and wherein the biasing member is partially-disposed within the retainer block.

5. The removable component according to claim 4, wherein, an exposed portion of the biasing member extends from the retainer block, the exposed portion of the biasing member configured to contact the finger ring portion of the grasping member upon pivoting of the grasping member towards the stored position to bias the grasping member against further movement towards the stored position.

6. The removable component according to claim 4, wherein, in the stored position of the grasping member, the finger ring portion is disposed about the retainer block in surrounding relation therewith.

7. A surgical system, comprising:
    a surgical instrument defining an internal compartment and a door movable between an open position and a closed position for providing access to the internal compartment and closing the internal compartment; and
    a removable component, including:
        a housing defining a first end and a second end, the housing configured for insertion into the internal compartment of the surgical instrument led by the first end thereof;
        a grasping member including a finger ring portion, at least one hinge leg, and an extension portion interconnecting the finger ring portion and the at least one hinge leg, the grasping member pivotably coupled to the housing at the second end of the housing via the at least one hinge leg, the grasping member pivotable about the at least one hinge leg and relative to the housing between a presented position, wherein at least a portion of the grasping member is spaced-apart from the second end of the housing, and a stored position, wherein the grasping member is approximated relative to the second end of the housing; and
        a biasing member disposed between the grasping member and the second end of the housing, the biasing member configured to bias the grasping member towards the presented position,
    wherein, upon moving the door of the surgical instrument to the closed position with the removable component disposed within the internal compartment, the door urges the grasping member towards the stored position against the bias of the biasing member.

8. The surgical system according to claim 7, wherein the surgical instrument further includes a lock assembly configured to lock the door in the closed position upon movement of the door to the closed position.

9. The surgical system according to claim 8, wherein, with the door locked in the closed position with the removable component disposed within the internal compartment, the biasing member is disposed in a loaded state.

10. The surgical system according to claim 8, wherein the lock assembly further includes a release button, the release button selectively depressible to unlock the door from the closed position.

11. The surgical system according to claim 10, wherein, upon depression of the release button to unlock the door, the grasping member is configured to bias the grasping member towards the presented position, thereby urging the door towards the open position.

12. The surgical system according to claim 7, wherein the removable component is a battery pack configured to provide power to the surgical instrument.

13. The surgical system according to claim 12, wherein the battery pack includes at least one electrical contact disposed at the first end of the removable component, the at least one electrical contact configured to electrically couple to a corresponding at least one electrical contact of the surgical instrument upon insertion of the removable component into the internal compartment for providing power to the surgical instrument.

14. The surgical system according to claim 7, wherein the finger ring portion is configured to facilitate manipulation of the removable component.

* * * * *